United States Patent [19]

Guelta et al.

[11] Patent Number: 5,059,348

[45] Date of Patent: Oct. 22, 1991

[54] METHOD FOR MEASURING THE EFFICIENCY OF GAS MASK FILTERS

[75] Inventors: Mark A. Guelta, White Marsh; Hugh R. Carlon, Fallston, both of Md.

[73] Assignee: The United States of America as represented by the Secretary of the Army, Washington, D.C.

[21] Appl. No.: 636,161

[22] Filed: Dec. 31, 1990

[51] Int. Cl.$^5$ .............................................. G01N 32/00
[52] U.S. Cl. .................. 252/408.1; 252/305; 73/40; 261/18.1
[58] Field of Search ................. 252/408.1, 305; 73/40; 261/18.1

[56] References Cited

U.S. PATENT DOCUMENTS

| H267 | 5/1987 | Carlton et al. | 356/336 |
| 4,914,957 | 4/1990 | Dougherty | 73/40 |
| 4,917,830 | 4/1990 | Ortiz et al. | 261/18.1 |
| 4,963,289 | 10/1990 | Ortiz et al. | 252/305 |

*Primary Examiner*—Robert L. Stoll
*Assistant Examiner*—N. Bhat
*Attorney, Agent, or Firm*—Anthony T. Lane; Edward Goldberg; Edward F. Costigan

[57] ABSTRACT

An improved process of passing an aerosol mixture through a filter. The aerosol is generated by nebulization of the mixture prior to penetration of the filter. The aerosol mixture being in %, by volume, of about:

| % | Chemical |
|---|---|
| 70–76 | isostearic acid |
| 6–7 | isopalmitic acid |
| 7–11 | myristic acid |
| 4–5 | palmitic acid. |

5 Claims, 4 Drawing Sheets

LOW PRESSURE FLOW SCHEMATIC

HIGH PRESSURE FLOW SCHEMATIC

FIG. 2 LOW PRESSURE FLOW SCHEMATIC

METHOD FOR MEASURING THE EFFICIENCY OF GAS MASK FILTERS

GOVERNMENTAL INTEREST

The invention described herein may be made, used or licensed by or for the Government for governmental purposes without the payment to us of any royalties thereon.

FIELD OF USE

An improved method of testing a filter for gas masks, respirators, and personnel protective equipment.

BACKGROUND OF THE INVENTION

The present invention relates to a method for the generation of a nearly monodispersed aerosol in filter-testing machines.

For several decades, the U.S. Army has produced hot smokes using dioctyl phthalate (DOP) as the standard material in the performance of nondestructive gas mask and filter serviceability testing. Hot smokes are aerosols produced using a method of thermally-generated vaporization and recondensation (self nucleation) of particles. Heated air passes across the surface of a heated liquid (DOP), cooler air then merges with the vapor, causing recondensation of an aerosol or "hot smoke."

Recently, a new generation of smoke penetrometers have been developed which utilize the generation of cold smokes or cold aerosols. Cold smokes are aerosols generated by the process of pressurized nebulization aerosol generation. This process produces an aerosol which is thermally more stable than a hot smoke. The U.S. Army Surgeon General has designated DOP as a suspected carcinogen and has prohibited or severely restricted its use in smoke-generating machines used to test U.S. Army masks, respirators, filters and other personnel protection equipment.

PRESENT INVENTION

The present invention is superior to the previous method in that it employs a candidate mixture as a replacement for dioctyl phthalate (DOP), which is a suspected carcinogen. In the following discussion, the term "Candidate Material" will be used to designate an aerosol composition made up of the following in %, by volume, of about: 70-76% isostearic acid, 6-7% isospalmitic acid, 7-11 myristic acid, and 4-5% palmitic acid. The candidate mixture is manufactured by Henkel Corporation, Emery Group, 11501 Northlake Drive, P.O. Box 429557, Cincinnati, Ohio 45247. The candidate mixture has been identified by us as a thermally stable material of low toxicity.

The Model 8110 Automated Filter Tester is a state-of-the-art "cold smoke" machine manufactured by TSI, Incorporated, 500 Cardigan Road, P.O. Box 64394, St. Paul, Minn. 55164. It is widely used in filter penetration testing. We shall first give an operating description of the equipment, and then describe our process and material comprising our invention for use with this equipment.

SYSTEM OVERVIEW

Figure 1:
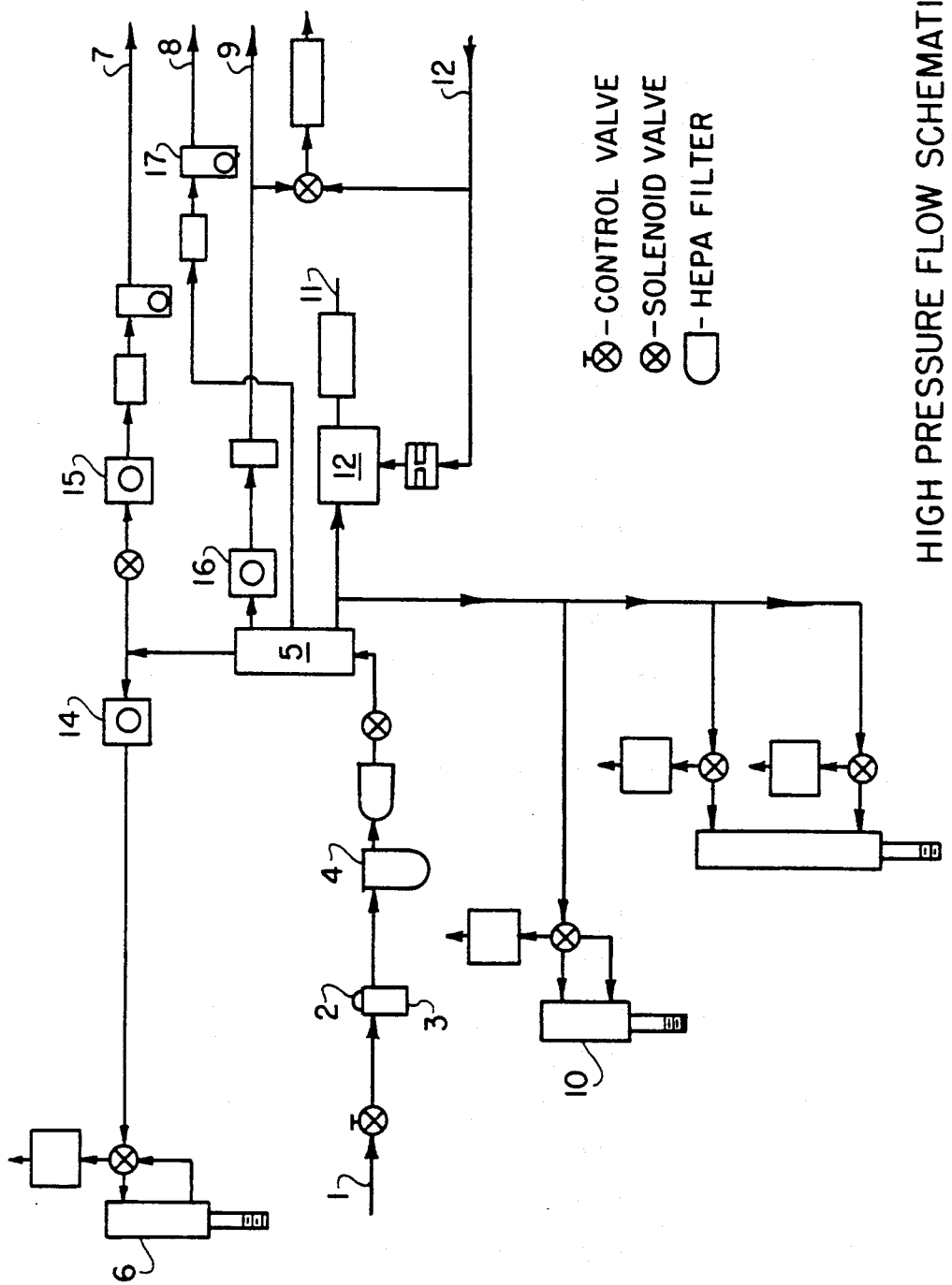
FIG. 1 is a diagram of the high pressure flow system used to operate the 8110 pneumatic switches and valves, and supply air to other system components.

The TSI, Inc. Model 8110 Automated Filter Tester (AFT) is designed to measure filter penetrations and pressure drops for filter canisters, filter media, respirator cartridges, and disposable respirators to penetrations as low as 0.01%, for low aerosol concentrations, and down to 0.001% for high concentrations. Pressure drops up to 150 millimeters of water can be measured.

The AFT uses a compressed air nebulizer to generate submicron aerosols in solid or liquid form which serves as the challenge aerosol for measuring filter penetration. The concentration level of challenge aerosol can be varied from a mass concentration of 12 milligrams per cubic meter ($mg/m^3$) up to 100 $mg/m^3$.

The aerosol is transported to a mixing/drying chamber where dilution air is added. The dried aerosol is then transported either to an exhaust port on the outside of the AFT or to the filter chuck. The aerosol passes through a orifice on the way to the filter holder where a pressure measurement is made and converted to flow rate. After the aerosol passes through the filter holder, a portion travels to the photometer, and the remaining aerosol exhausts out of the AFT.

The AFT uses a solid-state photometer as the particle detector. The photometer uses a 5 milliwatt laser diode as the light source and a photodetector for measuring the scattered light. Four different amplifier gain settings on the photometer electronics allows the AFT to measure concentrations through a wide dynamic range. These gain settings are automatically selected by the AFT microprocessor. A sheath air system in the photometer is used to prevent the challenge aerosol from contaminating the light scattering chamber. The photometer has a three position switching valve mounted on the inlet to allow the photometer to sample from three independent locations. The photometer samples clean purge air when the AFT is idle. During a filter test, the photometer samples the aerosol concentration downstream of the filter and then upstream. The dynamic range of the photometer enables the AFT to measure filter penetrations down to 0.01% and as low as 0.001% when higher concentrations of aerosol are generated.

The AFT has three modes of operation; Standard Test Mode, Flow Set-up Mode, and Loading Test Mode. The Flow Set-up Mode is used to monitor and adjust the flow rate through the filter. The Standard and Loading Test Modes measure the filter penetration, pressure drop, and flow rate. The loading test differs from the standard test in that it runs continuously to monitor the filter characteristics over time.

The AFT uses a dedicated microprocessor (CPU) to control the entire tester. This CPU controls all the valving and data collection. The operator simple inserts the filters in the filter chuck and closes the chuck. The CPU will run the test to completion and open the chuck when all the data is collected. A three line LED display on the AFT front panel displays filter flow rate in liters/minute, pressure drop in millimeters of water, and penetration in percent. The AFT was designed for easy maintenance. All components exposed to aerosols are easily accessible and can be cleaned in a short amount of time.

SYSTEM OPERATION

FIG. 1

Compressed air enters the system at 60 psi with a minimum flow rate of 7 standard cubic feet per minute (SCFM) (1, FIG. 1). After passing through a regulator, desiccator, and prefilter (2,3,4, FIG. 1), the air enters the air distribution manifold (5, FIG. 1). The air distribution manifold distributes air to the filter chuck cylinder (6, FIG. 1), aerosol atomizer (7, FIG. 1), dilution air (8, FIG. 1), photometer (9, FIG. 1), drying/mixing chamber (10, FIG. 1), or exhaust port (11, FIG. 1). A vacuum pump draws (13, FIG. 1) air from the photometer outlet (12, FIG. 1) and air distribution manifold to be exhausted.

Air is supplied to operate the chuck at pressures up to 60 psi., generally 40 psi is sufficient to hold most filter cartridges. Air pressure to the chuck is controlled by an in-line regulator (14, FIG. 1). Air supplied to the aerosol generator is regulated from 0-30 psi (15, FIG. 1). The photometer purge air regulator (16, FIG. 1) is set to 10 psi. Dilution air supplied to the mixing/drying chamber is controlled by (17, FIG. 1) a in-line flowmeter. Air supplied to valve assemblies for mixing chamber and photometer switching valve assemblies is supplied at 60 psi, this is regulated by the air intake regulator (2, FIG. 1).

FIG. 2

Figure 2:
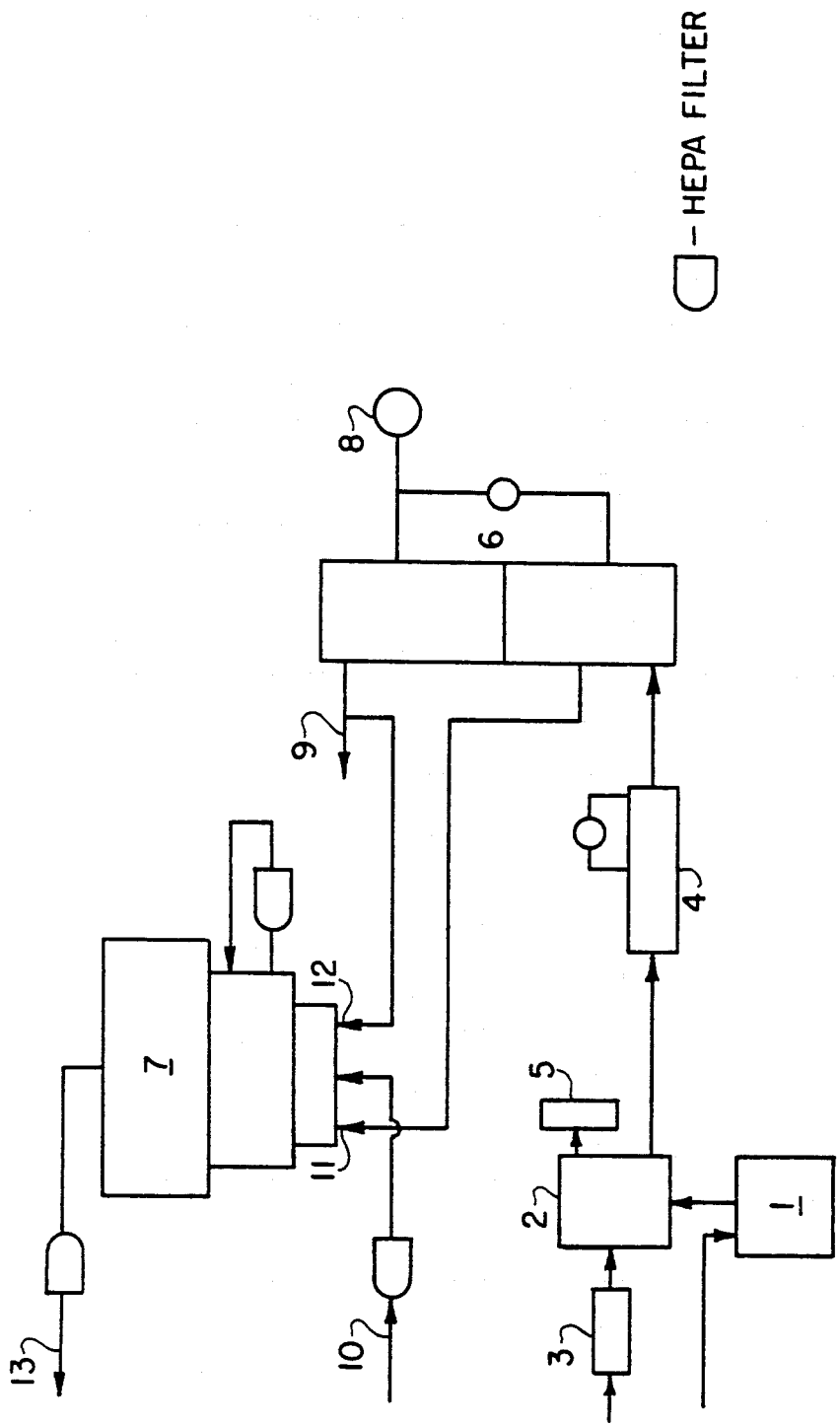
FIG. 2 is a diagram showing flow paths for aerosol generation, measurement, and filter test flows in the TSI 8110 AFT.

Air flows from the air distribution manifold to the aerosol generator (1, FIG. 2), atomizer air is regulated to 20 psi for low concentration mode, or 30 psi for high concentration mode. In the low concentration mode, the 20 psi of air is supplied to a single nebulizer for aerosol generation. In the high concentration mode, 30 psi of air is supplied to 4 nebulizers to generate a more concentrated aerosol. The aerosol flows from the aerosol generator to the aerosol drying/mixing chamber (2, FIG. 2).

Dilution air comes from the air distribution manifold through a in-line heater (3, FIG. 2) used to heat the dilution air when a salt aerosol is being generated. When producing candidate material aerosols the heater is not used. The dilution air mixes with the aerosol from the aerosol generator to ensure a uniform concentration. The diluted aerosol leaves the mixing chamber and travels through a in-line flow controller (4, FIG. 2) to the chuck. Between tests, excess aerosol is exhausted from the mixing chamber to the exhaust manifold where it leaves the instrument (5, FIG. 2).

When the chuck is closed, aerosol is free to flow through the chuck (6, FIG. 2) and the filter material to be tested. A portion of the aerosol from the upstream side of the chuck flows to the scattering chamber (7, FIG. 2). A pressure gauge (8, FIG. 2) measures pressure differential between the upper and lower portion of the chuck to indicate pressure drop across the filter during tests. Aerosol leaving the downstream portion of the chuck is divided, a portion of the air goes to the scattering chamber, the rest is exhausted (9, FIG. 2).

Three streams of air enter the scattering chamber through the photometer switching valve assembly. Clean, filtered air from the air distribution manifold enter the manifold and scattering chamber (10, FIG. 2) between filter tests to clear aerosol from the chamber allowing the photometer to establish a baseline reading. Aerosol from the upstream side of the test chuck enter the photometer switching assembly (11, FIG. 2) and the scattering chamber during the test to establish a 100 percent aerosol concentration reading. After the 100 percent level is established, purge air clears the aerosol from the chamber. Aerosol from the downstream side of the test chuck is then introduced into the scattering chamber (12, FIG. 2). A percent of 100 reading is taken of the air which passes through the filter material being tested. Purge air and test aerosol is exhausted after leaving the scattering chamber (13, FIG. 2).

The microprocessor fully automates the test procedures. The test mode, flow rates, and length of test can be set up using the key pads on the instrument's control panel. Once set up, the operator only inserts the filter media and closes the chuck; from there the test is controlled by the microprocessor. An LED display gives a real time indication of the flow rates, pressure drop across the media, and percent penetration. At the end of the test, the chuck automatically opens; a report of the test results may be printed by the 8110's built-in printer.

For the purposes of qualifying the aerosol produced by the 8110, a TSI Differential Mobility Particle Size Analyzer (DMPS) was used to characterize the aerosol output. A sample of the aerosol was taken at the exhaust port of the 8110. The aerosol was diluted to measurable concentrations using a TSI model 3302 capillary diluter. The DMPS samples the aerosol and reports the aerosol surface mean diameter and spread factor.

PREFERRED EMBODIMENT OR RECOMMENDED MACHINE SETTINGS

Due to the nature of the model 8110's operation, no alteration of machine settings are required when generating an aerosol of DOP or the candidate material. The following parameters were used to generate an aerosol in the low concentration mode using the candidate material.

| Low Concentration Mode: | |
| --- | --- |
| Nebulizer pressure | 20 psi |
| Dilution air flow rate | 180 LPM |

The machine settings above were found to produce a mass concentration of 12.9 mg/m$^3$, the surface area mean diameter was measured to be 0.201 microns with a spread factor of 1.388.

| High Concentration Mode: | |
| --- | --- |
| Nebulizer pressure | 30 psi |
| Dilution air flow rate | 150 LPM |

The machine settings used in the high mode were found to produce a mass concentration of 114.9 mg/m$^3$, the surface area mean diameter was measured at 0.203 $\mu$m, with a spread factor of 1.345. These specifications met or exceeded those obtained using DOP.

Figure 3:
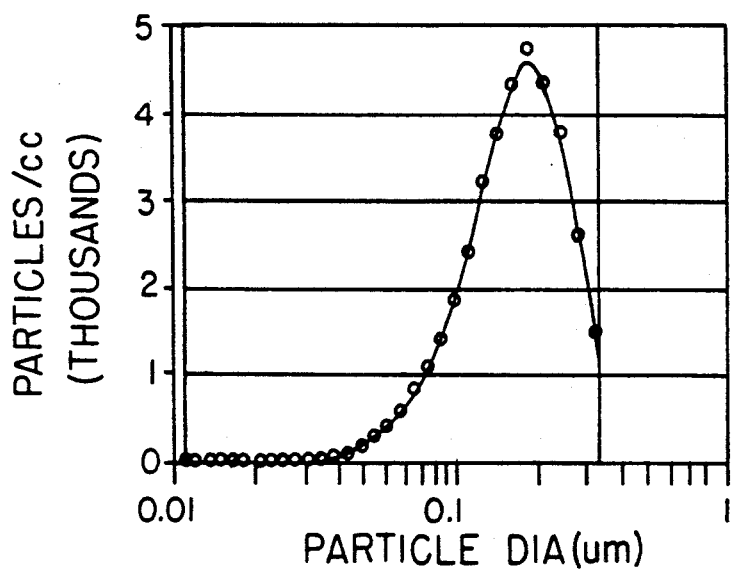
FIG. 3 is a graph showing the particle count distribution produced by the candidate material in the Model 8110 tester.
Figure 4:
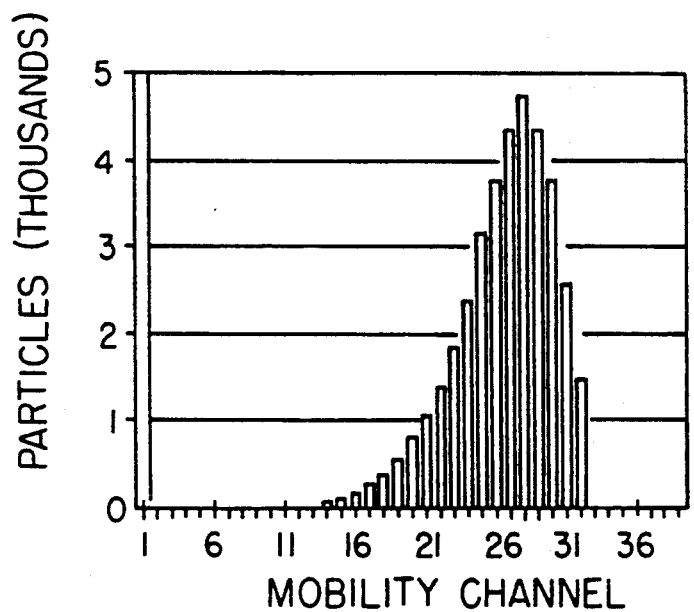
FIG. 4 is a graph showing the particle count distribution measured by the TSI Differential Mobility Particle Sizer.

The particle count distribution produced by our candidate or replacement material in the Model 8110 tester is shown in FIG. 3 vs. particle diameter in micrometers. The particle count distribution measured by the TSI Differential Mobility Particle Sizer that was used with the Model 8110 tester is shown in FIG. 4 vs. mobility channel number. These results are hereinafter discussed.

Our test data for this candidate or replacement material are discussed hereinafter in the specification. These data are discussed in connection with FIGS. 3 and 4.

| TSI DIFFERENTIAL MOBILITY PARTICLE SIZER | |
|---|---|
| SAMPLE EMERSOL 875 | SAMPLE AEROSOL FLOW RATE: 0.6 LPM |
| MODE: HIGH CONC. | MAXIMUM DIA. MEASURED: 0.337 |
| | MINIMUM DIA. MEASURED: 0.011 |
| MEAN SURFACE DIAMETER 0.203 | SPREAD 1.345 |

| Mobility Channel # | Diameter Midpoint (μm) | Number Concentration (part/cc) |
|---|---|---|
| 1 | .010 | 0 |
| 2 | .011 | 0 |
| 3 | .012 | 8.17 |
| 4 | .014 | 37.9 |
| 5 | .015 | 120.0 |
| 6 | .017 | 350/01 |
| 7 | .018 | 801.36 |
| 8 | .021 | 1646.05 |
| 9 | .023 | 3088.8 |
| 10 | .025 | 5213.22 |
| 11 | .028 | 8186.86 |
| 12 | .031 | 1.341E4 |
| 13 | .035 | 2.046E4 |
| 14 | .038 | 2.832E4 |
| 15 | .043 | 4.201E4 |
| 16 | .048 | 6.112E4 |
| 17 | .053 | 8.833E4 |
| 18 | .059 | 1.284E5 |
| 19 | .066 | 1.589E5 |
| 20 | .074 | 2.033E5 |
| 21 | .083 | 2.4 E5 |
| 22 | .093 | 2.906E5 |
| 23 | .104 | 3.704E5 |
| 24 | .117 | 6.892E5 |
| 25 | .132 | 1.028E6 |
| 26 | .15 | 1.321E6 |
| 27 | .17 | 1.495E6 |
| 28 | .193 | 1.464E6 |
| 29 | .221 | 1.257E6 |
| 30 | .253 | 9.659E5 |
| 31 | .291 | 6.783E5 |
| 32 | .337 | 3.49 E5 |
| 33 | .391 | 0 |
| 34 | .457 | 0 |

Figure 5:
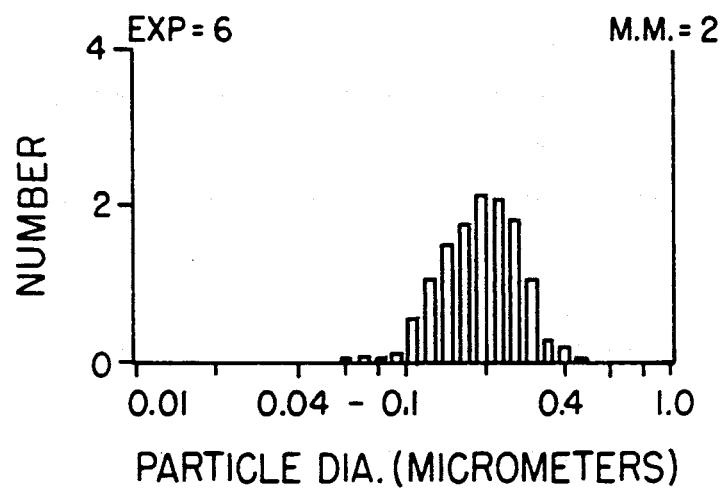
FIG. 5 is a graph showing distribution taken by the manufacturer, TSI, Inc., using DOP in the Model 8110 machine.

The data for our candidate material, as shown above, indicate that our material produces very satisfactory results in the Model 8110 machine. For comparison, FIG. 5 shows a typical distribution (directly comparable to FIG. 3) taken by the manufacturer, TSI, Inc., using DOP in their Model 8110 machine. It is seen clearly that our material (FIG. 3) and DOP (FIG. 5) both produce smoke aerosols with mean particle diameters near 0.2 micrometers, and that our material produces a narrow, symmetrical distribution of particle sizes. Thus our material can replace the suspected carcinogen, DOP, directly in the Model 8110 and, using our process and procedures, will allow filter tests at least as rigorous as those with DOP to be performed.

In the past, we discussed our materials, process, and procedure inventions for the use of our replacement materials in a "hot pot" machine, the Model TDA-100 manufactured by Air Techniques, Inc., (ATI) in Baltimore, Md. TSI is marketing the Model 8110 Automated Filter Tester (AFT) as a cold smoke alternative to the TDA-100 hot smoke machine.

Therefore, it is important to show here that in filter penetration testing, the Model 8110's performance with DOP is comparable to the Q-127/TDA-100's performance using DOP. Since our material has been shown to perform at least as well as DOP, and often better, in both of these machines, we thus show that our material will give comparable percent filter penetration results in both machines.

Figure 6:
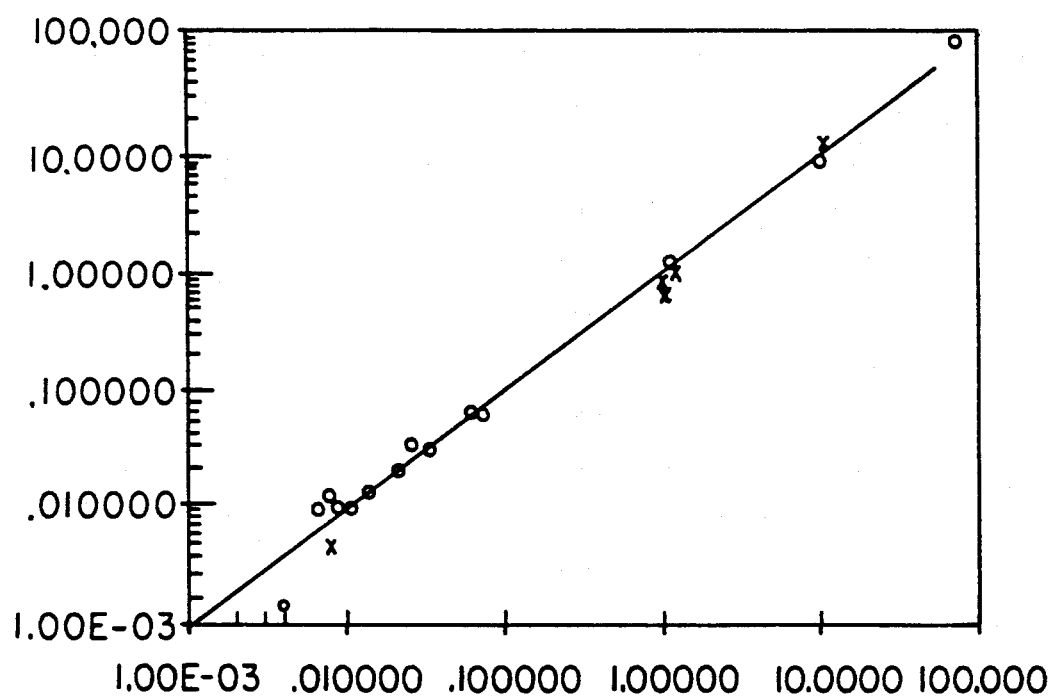
FIG. 6 is a graph showing comparison data of the Model 8110 and a Q127 tester.

Comparison data of the Model 8110 and a Q-127 tester (ATI's TDA-100) is shown in FIG. 6. Testing of filter media with well-known and consistent efficiencies was performed. The graph shows the efficiencies measured by the Q-127 tester on the horizontal axis. The vertical axis gives the efficiency measured by TSI's Model 8110 Automated Filter Tester. The data points allow a straight line to be formed, giving basically a one-to-one correlation for the testing performed. The tests were made using DOP as the challenge aerosol.

The data for our candidate material, as shown, indicates that our material produces very satisfactory results in the Model 8110 machine. It is seen clearly that our material and DOP both produce smoke aerosols with mean particle diameters near 0.2 micrometers, and that our material produces a narrow, symmetrical distribution of particle sizes. Thus, our material can replace the suspected carcinogen, DOP, directly in the Model 8110 and, using our process and procedures, will allow filter tests at least as rigorous as those with DOP to be performed.

What is claimed is:

1. In an improved process of passing a prior nebulized aerosol mixture through a filter, and thereafter measuring the filter efficiency the improvement consisting essentially of said aerosol being in %, by volume, of about:

| % | Chemical |
|---|---|
| 70–76 | isostearic acid |
| 6–7 | isopalmitic acid |
| 7–11 | myristic acid |
| 4–5 | palmitic acid. |

2. The process of claim 1 wherein the mass concentration of said aerosol at said filter is 114.9 mg/m$^3$.

3. The process of claim 1 wherein said filter efficiency measuring is done by light-scattering means.

4. The process of claim 1 wherein the aerosol mixture surface area mean diameter is about 0.203 microns.

5. The process of claim 1 wherein the aerosol mixture factor is about 1.345.

* * * * *